United States Patent
Shah

[19]

[11] Patent Number: 5,837,444
[45] Date of Patent: Nov. 17, 1998

[54] ISLET CELL TRANSPLANTATION MACHINE FOR DIABETES CURE

[76] Inventor: Kumarpal A. Shah, 28 Ridge Rd., Searingtown, N.Y. 11507

[21] Appl. No.: 680,795

[22] Filed: Jul. 16, 1996

[51] Int. Cl.[6] .............................. C12Q 1/00; C12M 3/08
[52] U.S. Cl. .............................. 435/4; 210/196; 422/101; 435/284.1; 435/294.1; 435/297.1; 435/297.2; 435/297.4; 435/306.1; 435/308.1
[58] Field of Search ........................ 422/101; 435/294.1, 435/297.2, 308.1, 4, 284.1, 297.1, 297.4, 306.1; 210/196

[56] References Cited

U.S. PATENT DOCUMENTS

| | | | |
|---|---|---|---|
| 4,036,698 | 7/1977 | Bush et al. .......................... | 435/297.2 |
| 4,406,786 | 9/1983 | Hein .................................... | 422/101 |
| 4,868,121 | 9/1989 | Scharp et al. ...................... | 435/268 |
| 5,079,160 | 1/1992 | Lacy et al. ......................... | 435/268 |
| 5,322,790 | 6/1994 | Scharp et al. ...................... | 435/268 |
| 5,447,863 | 9/1995 | Langley ............................... | 435/268 |
| 5,459,054 | 10/1995 | Skjak-Braek et al. ............. | 435/372 |

*Primary Examiner*—David Saunders
*Attorney, Agent, or Firm*—Shenier & O'Connor

[57] ABSTRACT

An apparatus for collecting a subpopulation of cells larger than a predetermined size from a collagenase distended organ by circulating fluid through a closed loop system. The closed loop system includes a digesting chamber to liberate cells from the organ, a cell collection chamber, and a filter adjacent the cell collection chamber for retaining cells larger than the predetermined size. The circulating fluid transports liberated cells through the cell collection chamber to the filter. Subsequently, the cells on the filter are flushed back into the cell collection chamber by a density medium. A tube then withdraws the desired subpopulation of cells from the cell collection chamber.

18 Claims, 2 Drawing Sheets

ISLET CELL TRANSPLANTATION MACHINE FOR DIABETES CURE

BACKGROUND OF THE INVENTION

This invention relates, in general, to apparatus for cell transplantation technology, and, in particular, to apparatus for islet cell transplantation for the cure of Diabetes Mellitus

DESCRIPTION OF THE PRIOR ART

In the prior art various types of instruments for cell isolation have been proposed. For example, U.S. Pat. No. 5,079,160 discloses a method of obtaining purified, well-defined cell population from intact organs which uses the digestion of the distended organ with suitable proteolytic enzymes and harvest of the cell subpopulation by screening the effluent from the treatment of the organ with physiologically compatible medium by a filtration screen which permits the passage of the desired cells, but prevents the passage of large particles.

U.S. Pat. No. 5,447,863 discloses a method and apparatus to concentrate and purify islets of Langerhans from a tissue suspension containing islets and tissue fragments. The tissue suspension is flowed through an inclined channel such that laminar flow is established. The islets settle toward the bottom and are drawn out.

U.S. Pat. No. 5,322,790 discloses a method of producing intact islets of Langerhans using a mixture of Hank's solution and 10% by volume fetal calf serum to ductally distend the human pancreas. The exocrine tissue of the pancreas is digested at about 37° C. by an enzyme preparation of collagenase, trypsin and proteolytic enzyme preset in the mixture at a level of about 0.2% by weight.

U.S. Pat. No. 4,868,121 discloses a method of producing intact islets of Langerhans using a mixture of Hank's solution and 10% by volume fetal calf serum to ductally distend the human pancreas. The exocrine tissue of the pancreas is digested at about 37° C. by an enzyme preparation of collagenase, trypsin and proteolytic enzyme preset in the mixture at a level of about 0.2% by weight. The digested pancreas is comminuted, filtered and intact islets are recovered.

As shown by the above cited prior art patents, islet cell transplantation has evolved over the last decade. This technology is a conceptual advance over organ transplantation and can replace pancreas transplantation, thereby eliminating many of the drawbacks and side effects of pancreas transplantation.

In a pancreas transplant a donor pancreas is obtained and directly transplanted into a patient. Infection and the risk of rejection is always present in such an operation. However, in islet cell transplantation the objective is to transplant live, viable islet cells and discard 99% of the exocrine pancreas which is useless. In such a procedure, the dangers associated with a pancreas transplant are virtually eliminated. In islet cell transplantation the pancreas is processed in a laboratory to liberate and purify the islet cells. The cells are then encapsulated to prevent destruction by the host immune attacks (immunoisolation) and then transplanted into a patient. Islet cell transplantation has been hailed as a cure for Diabetes Mellitus This is a disease that affects more than 3% of the world population and is a major public health problem. It is associated with an increase in renal failure, blindness, heart attacks, strokes, hypertension and amputations. In a 1992 study, it was noted that 3% of the diabetic patients accounted for 15% of the health care costs, and amounted to a staggering 100 billion dollars. These high costs indicate a failure, using conventional approaches, to control blood sugar levels in patients and to cure the underlying disease and the morbidity associated with this disease.

The most widely used approach to isolate islet cells is the method and apparatus disclosed in the Lacey et al patent, (U.S. Pat. No. 5,079,160). In pancreas transplantation the cure of type 1 diabetes is feasible with ½ to 1 pancreas while the transplantation of islet cells using known technology requires as many as 8 pancreas. Thus there is an increase of up to 16 fold in the number of pancreas needed to realize a sufficient supply of islets. Clearly major improvements are needed in the current methods of islet cell isolation procedures.

SUMMARY OF THE INVENTION

The present invention utilizes the basic concept of filtration. A dual channeled vacuum-pressure pump is used across two chambers to generate a continuous circulation of fluid. The first chamber is used to digest collagenase distended pancreas at 37° C., while the second chamber is used to concentrate and purify the islet cells at 4° C. The following additional improvements are incorporated to reduce bioburden, improve immunoprotection of viable cells and to automate laboratory components of islet cell transplantation.

1) Use of a dry incubator to reduce water contamination risk.

2) Eliminating the need for mechanical shaking to reduce airborne contamination.

3) The use of aseptic vacutainer port for aseptic sample aspiration for various studies and to reduce the risk of infection.

4) The use of a Leuco-absorb filter to remove passenger leucocytes, thereby reducing immunogenicity and the risk of infection from leucotrophic viruses.

5) The use of A/G technology hollow fibers without macrovoids to improve tensile strength and reduce the risk of breakage of the hollow fibers.

6) The use of Na Aliginate with high 'G' content to immunoisolate islet cells and to reduce the risk of fibrosis of hollow fibers after being implanted.

7) The use of gentle, atraumatic cell separation technique such as velocity sedimentation at unit gravity to purify islet cells in the cell collection chamber. This allows further automation and integration of organ digestion, cell separation and purification. Purified islet cells can be conveniently syringe extruded and gelled inside hollow fibers, either manually or by an automated approach.

It is an object of the present invention to provide an improved apparatus for islet cell transplantation that is cost effective and clinically safe to use.

It is an object of the present invention to provide improved apparatus for islet cell transplantation that obviates the problems associated with the prior art apparatus.

These and other objects and advantages of the present invention will be fully apparent from the following description, when taken in connection with the annexed drawings.

DESCRIPTION OF THE PREFERRED EMBODIMENT

Figure 1:
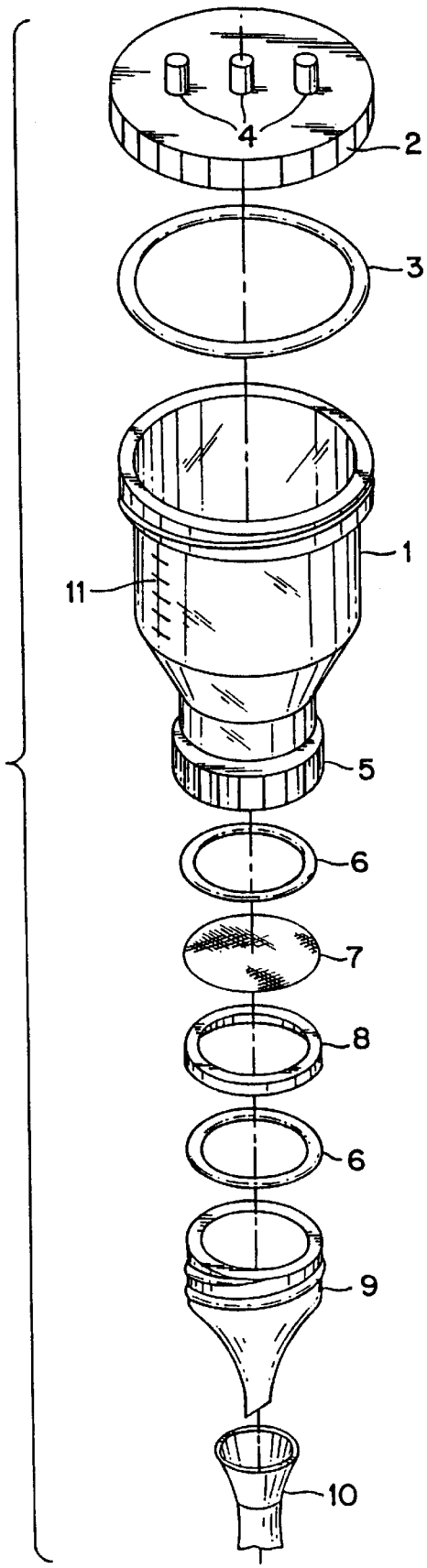
FIG. 1 is a perspective, exploded view showing the digestion and cell collection chambers of the present invention.

Referring now to the drawings in greater detail, FIG. 1 shows an exploded view of the digestion chamber 1 of the present invention. The digestion chamber 1 is essentially the same as the cell collection chamber, except as noted below, and therefore, a view of one chamber will show all the essential details of both chambers. The digestion chamber has a container 1 which is preferably made of clear, biocompatible polysulfone material, and is autoclavable and reusable. The chamber size is approximately 500 ml and has graduations 11 along the side.

A cover 2 is attached to the top of the chamber, for example by screw threads (not shown) and is sealed by means of a conventional O-ring 3. The cover 2 has three ports 4, for a purpose to be described below. The bottom of the chamber 1 is open and has a bottom cover 5. It should be noted that the bottom cover is shown as attached to the bottom of the chamber and the O-rings 6, the filter 7 and the support plate 8 for the filter are shown outside the bottom cover 5 only for illustration purposes. Actually, the O-rings 6, the filter 7 and the support plate 8 for the filter are inside the bottom cover which holds the various elements in place and also secures the funnel 9. Attached to the bottom of the funnel 9, by any conventional means is a vacuum adaptor 10 which secures the funnel to the tubing 12, as shown in FIG. 2.

Figure 2:
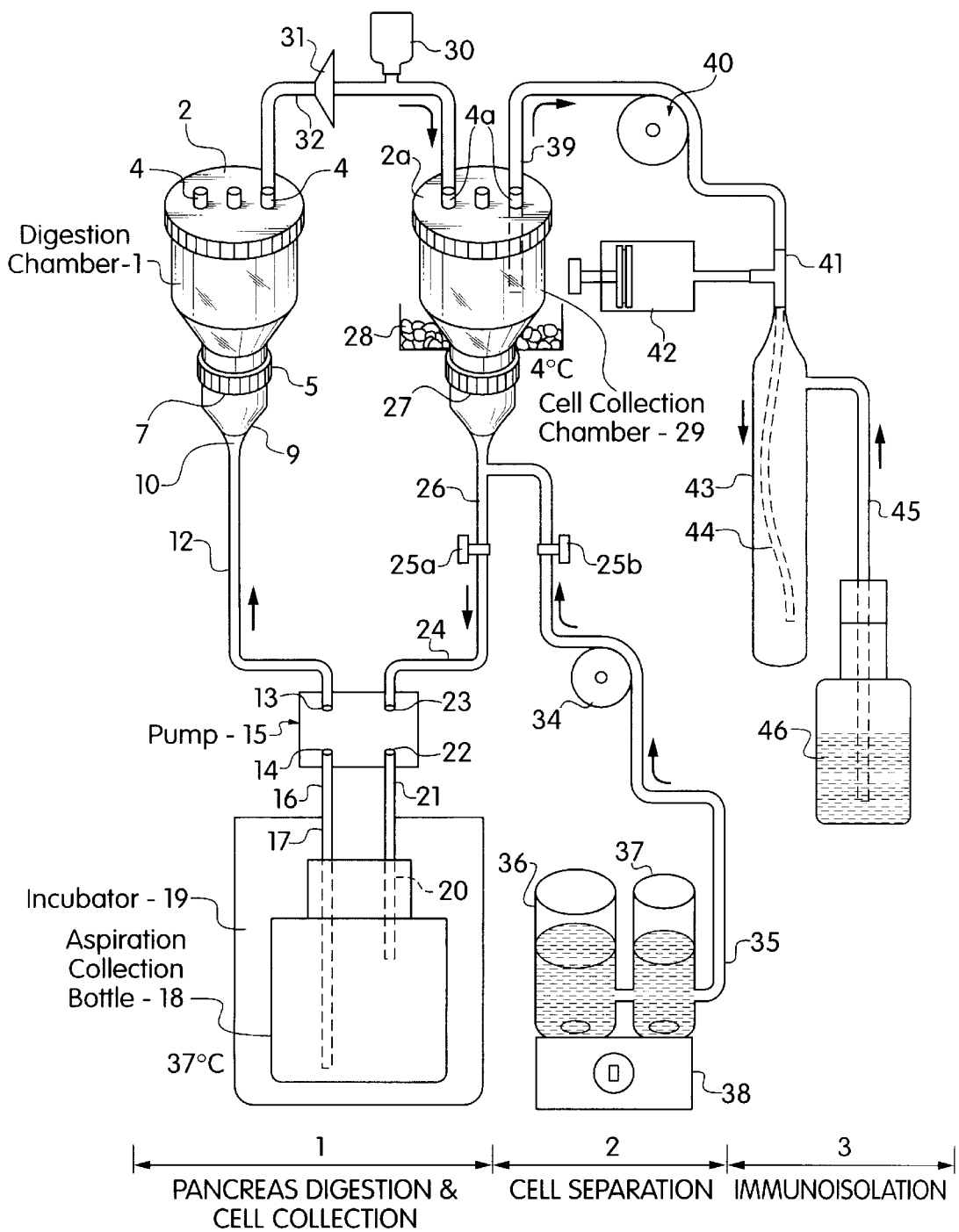
FIG. 2 is a schematic view of the present invention showing a three step approach to automate and integrate various laboratory components of islet cell transplantation.

Referring now to FIG. 2, the positioning and connection of the digestion and cell collection chambers 1 and 29 are shown. The two chambers on the top are connected by neoprene tubing 32 connected to respective ports 4 and 4a. A leukocyte filter 31 and a sampling port 30 are interposed between the connections to the chambers 1 and 29. The bottom of the chamber 1 is connected through the funnel 9 to approximately four feet of neoprene tubing 12, to the outlet port 13 of vacuum pressure pump 15. The inlet port 14 of the pump 15 is connected to approximately three feet of neoprene tubing 16. The other end of this tubing is attached to port 17 of the aspiration-collection bottle 18. The aspiration-collection bottle 18 is housed inside a dry incubator 19 at a temperature of 37° C. The port 20 of the aspiration-collection bottle 18 is connected to approximately three feet of neoprene tubing 21. The other end of this tubing is connected to outlet port 22 of the vacuum-pressure pump 15. The inlet port 23 of the vacuum-pressure pump 15 is connected to four feet of neoprene tubing 24. The other end of this tubing is connected to the arm of inverted "Y" adapter 26. Claps 25a and 25b are interposed below "Y" adapter 26 to regulate fluid flow.

Element 27 is a screening filter placed in the bottom of chamber 29 to permit the collection of islet cells between 50–450 micron size and pass cell debris less than 50 micron size. Collected islet cells are cooled to 4° C. by an ice bag containing device 28.

The other arm of the inverted "Y" adapter 26 is connected to tubing 35. Element 34 is a variable speed peristaltic pump that regulates the flow of density media to the chamber 29. Density gradient apparatus 36 and 37 are placed on the magnetic stirrer 38.

Inside chamber 29 is a cell aspiration tubing 39. Cells are aspirated by the variable speed peristaltic pump 40 and transported via three way valve 41 to a 50 ml syringe 42. The cells are mixed with Na alginate present in the syringe and extruded into the lumen of the hollow fiber housed in immunoisolation chamber 43. Element 46 is an aspiration bottle containing $CaCl_2$ which is aspirated by way of tubing 45 into immunoisolation chamber 43.

The apparatus shown in FIG. 2 is assembled after being sterilized and primed. The top cover 2a of the cell collection chamber 29 is removed and the chamber is filled with 500 ml of Hank's balanced solution. Then the aspiration-collection bottle 18, of 1–2 liter capacity, is filled with Hank's balanced solution. The funnel 9 at the bottom of the digestion chamber 1 is detached from the adapter 10 and is directed to a waste container (not shown) and the vacuum-pressure pump 15 is started. This causes negative suction in cell collection chamber 29, drawing Hank's solution from the chamber 29, across the filter 27 into the aspiration-collection bottle 18.

The fluid is warmed to 37° C. by an incubator 19. The fluid from the aspiration-collection bottle 18 exits through tubing connection 17. A positive pressure is exerted to drive fluid through the adapter 10. Approximately 10–20 ml of Hank's solution is allowed to drip out, then the funnel 9 is reattached to the adapter 10. Hank's solution will enter the chamber 1 through positive pressure from the pump 15. At this point the pump is stopped. The temperature of the Hank's solution is allowed to reach 37° C.

Collagenase distended pancreas is then loaded into chamber 1 from the top, and the top cover 2 is secured tightly. The vacuum-pressure pump 15 is started and positive pressure is exerted in chamber 1, and simultaneously negative pressure is exerted in chamber 29. This causes the fluid to circulate between chamber 29, aspiration-collection bottle 18, and chamber 1 where the fluid enters at 37° C.

Once the chamber 1 is filled, the fluid will move from chamber 1 to chamber 29 across the tubing 32 which bridges both chambers through ports 4 and 4a. A continuous recirculation of fluid is thus established. As the collagenase distended pancreas in chamber 1 is digested at 37° C., liberated cells will flow through port 4 into tubing 32. Wandering leucocytes are adsorbed in the leucoabsorb filter 31 and remaining cells enter chamber 29.

Intermittent samples of cells and fluid can be obtained through vacutainer port 30 for various studies. Cells exiting chamber 29 get deposited on filter 27, whose filter pore size is 50 microns. This allows islet cell of 50–450 micron size to be deposited on top of the filter. Smaller size cells and debris pass through filter 27 and are deposited in the aspiration-collection bottle 18. Reentry of debris into chamber 1 is blocked by interposing filters of 0.2 and 10 micron pore size between chamber 1 and tubing 17.

Once digestion is complete (approximately 30–45 minutes), the vacuum-pressure pump is turned off. The draining of fluid from chamber 29 to aspiration-collection bottle 18 is blocked by clamp 25a. Cells collected by filter 27 in chamber 29 are further purified without manually handling in any conventional manner. Peristaltic pump 34 is then started and clamp 25b is opened. This will draw density media solution from density gradient maker apparatus 36–37. The fluid will bottom lift cells deposited on filter 27 into chamber 29.

Then the pump is stopped, the top 2a of chamber 29 is opened and five glass balls are gently placed inside. The balls are of different colors, light weight and sterile. They are custom designed and calibrated at 20° C. to have a known density weight of 1.000, 1.050, 1.100, 1.150, and 1.200, respectively. Most islet cells will have a density in the range of 1.050 to 1.100. The cells are allowed to settle according to their size and density. This will take three to four hours. At this time a conventional transfer pipette (not shown) is introduced through port 4a to aspirate cell samples from different depths. The glass balls are used to monitor density and cell location.

Cell samples are stained with Dithiozone (DTZ) stain and examined under a light microscope (not shown) to help identify islet cells (stained dark brown). Once a desired cell band is identified, the tubing 39 is lowered to the desired depth as indicated by the glass balls. Cells are then aspirated by peristaltic pump 40. The cells are mixed in the 50 ml syringe 42 containing Na alginate solution with a high 'G' content. Cells are manually syringe extruded through 3-way adapter valve 41 into the A/G technology hollow fiber lumen 44.

The hollow fiber has a membrane which is cut off at 50 kD and are 1.5 to 2 mm in diameter, with a smooth outer surface. The hollow fiber is housed inside immunoisolation chamber 43, which is a glass pipette or burette. Container 46 contains 0.5 milimole/L of $CaCl_2$ solution and it is aspirated through tubing 45 into immunoisolation chamber 43 but outside the hollow fiber. Aspiration into the tubing is controlled by manually squeezing plastic container 46. $CaCl_2$ is diffused through the hollow fiber due to its smaller molecular weight and will cause gelling of the Na alginate inside the hollow fibers, which will gel suspend cells inside the hollow fibers. Once the cells are gelled inside the hollow fibers, the fibers are removed and cut appropriately aseptically. The fibers are now ready for transplantation into a patient's body.

The apparatus can be operated outside an operating room with due precautions and a portable laminar hood, either in a specially designed section, or in a laboratory. Prior to and after each run, the apparatus chamber and all tubing should be sterilized. Fresh filters should be used each time, and proper leak proof connections should be insured before each run. Face coverings, gloves, and gowns should be worn by all operators, who should be trained in proper instrument handling, sterile aseptic handling, and the handling of all electrical connections.

All chemicals, such as Hank's solution, fetal calf serum, DTZ stain, Collagenase enzyme, DNASE, Mg, $CaCl_2$, Na alginate with high 'G' content and density gradient media should be freshly prepared in appropriate quantity. The proper chemicals could be prepared before hand in kit form to facilitate islet cell isolation procedures. In addition, the temperature of fluid entering chamber 1 is maintained at 37° C. and chamber 29 is cooled to 4° C.

Although the apparatus for islet cell transplantation and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. An apparatus for collecting a subpopulation of cells larger than a predetermined size from a digested organ comprising:
   a closed loop system including (i) a chamber for digesting the organ to liberate cells, (ii) a cell collection chamber and (iii) a filter adjacent said cell collection chamber for retaining cells larger than the predetermined size;
   a first pump for circulating a physiologically compatible medium through the closed loop to transport the liberated cells through said cell collection chamber to said filter;
   a second pump for flushing the cells retained on said filter back into said cell collection chamber with a density medium;
   a tube for withdrawing the desired subpopulation of cells from said cell collection chamber; and
   a hollow fiber for containing the withdrawn cells.

2. The apparatus of claim 1, wherein said digesting chamber and said cell collection chamber are made of a transparent biocompatible polysulfone material.

3. The apparatus of claim 2, further comprising a first container holding a first portion of said density medium which comprises a first liquid, having a first density, and a second container holding a, second portion of said density medium which comprises a second, liquid having a second density different from said first density, wherein said two containers are coupled to said second pump to provide a density gradient.

4. The apparatus of claim 3, additionally comprising glass balls of different densities corresponding generally to the densities of said density gradient said glass balls being added to said density gradient to visually identify various density layers within the transparent cell collection chamber.

5. The apparatus of claim 4, wherein said tube withdraws cells from a particular density layer while maintaining a closed system.

6. The apparatus of claim 5, further comprising a peristaltic pump coupled to said tube, and
   wherein said tube is inserted into said cell collection chamber to an elevation corresponding with a particular density layer.

7. The apparatus of claim 3, comprising a magnetic stirrer coupled to said first and second containers.

8. The apparatus of claim 1, wherein said closed loop system further comprises:
   means for collecting particles smaller than the predetermined size which pass through said retaining means;
   means for heating the medium entering said digesting chamber to 37°C. and
   means for cooling said cell collection chamber to 4° C.

9. The apparatus of claim 1, wherein said closed loop system additionally includes a leukocyte filter for absorbing leukocytes from the medium passing from said digesting chamber to said cell collection chamber.

10. The apparatus of claim 1,
    wherein said first pump circulates medium through said filter in a first direction; and
    wherein said second pump introduces the density medium through the filter in a second direction opposite said first direction while maintaining a closed system.

11. The apparatus of claim 1, further comprising means for combining the withdrawn cells with Na alginate with a high 'G' content while maintaining a closed system.

12. The apparatus of claim 11, additionally comprising a syringe, wherein the cells and the Na alginate are placed into the hollow fiber lumen by the syringe while maintaining a closed system.

13. The apparatus of claim 12, further comprising an immunoisolation chamber containing the hollow fiber.

14. The apparatus of claim 13, further comprising a container coupled to said immunoisolation chamber for adding $CaCl_2$ to coat the hollow fiber and gel the Na alginate.

15. The apparatus of claim 12, wherein said hollow fiber is made of polysulfone.

16. The apparatus of claim 1, additionally comprising a vacutainer port in the closed loop between said digesting chamber and said cell collection chamber.

17. The apparatus of claim 3, wherein said second pump is a peristaltic pump.

18. An apparatus for isolating and collecting cells comprising:

- a digestion chamber including an open bottom, an open top and a first sealable top cap having at least one port;
- a first filter and a first connector securing said first filter to the open bottom of the digestion chamber;
- a pump connected to said first connector;
- a collection chamber including an open bottom, an open top and a second sealable top cap having at least one port connected to one of said ports of said first cap;
- a second filter and a second connector securing said second filter to the open bottom of said collection chamber, wherein said second connector is connected to said pump for establishing a circulatory flow from said second connector to said first connector;
- means for introducing a medium into said collection chamber through said second filter; and
- a hollow fiber and means for coupling another port of said second top cap to said hollow fiber lumen.

* * * * *